United States Patent
Toyota et al.

(10) Patent No.: US 9,955,717 B2
(45) Date of Patent: May 1, 2018

(54) NYSTOSE CRYSTAL-CONTAINING POWDER

(71) Applicant: MEIJI CO., LTD., Tokyo (JP)

(72) Inventors: Kenji Toyota, Kanagawa-ken (JP); Hiroki Ohara, Kanagawa-ken (JP)

(73) Assignee: MEIJI CO., LTD., Tokyo (JP)

( * ) Notice: Subject to any disclaimer, the term of this patent is extended or adjusted under 35 U.S.C. 154(b) by 207 days.

(21) Appl. No.: 14/441,920

(22) PCT Filed: Nov. 12, 2013

(86) PCT No.: PCT/JP2013/080533
§ 371 (c)(1),
(2) Date: May 11, 2015

(87) PCT Pub. No.: WO2014/073698
PCT Pub. Date: May 15, 2014

(65) Prior Publication Data
US 2015/0282511 A1    Oct. 8, 2015

(30) Foreign Application Priority Data

Nov. 12, 2012   (JP) ................... 2012-248358
Aug. 29, 2013   (JP) ................... 2013-177814

(51) Int. Cl.
| | | |
|---|---|---|
| *A23L 29/30* | (2016.01) | |
| *C07H 3/06* | (2006.01) | |
| *C07H 1/00* | (2006.01) | |
| *C12P 19/14* | (2006.01) | |
| *C12P 7/58* | (2006.01) | |
| *C12P 19/02* | (2006.01) | |
| *A61K 9/50* | (2006.01) | |

(52) U.S. Cl.
CPC ............. *A23L 29/30* (2016.08); *C07H 1/00* (2013.01); *C07H 3/06* (2013.01); *C12P 7/58* (2013.01);
(Continued)

(58) Field of Classification Search
CPC . A23L 27/33; A23L 29/30; C07H 3/06; C12P 19/14
(Continued)

(56) References Cited

U.S. PATENT DOCUMENTS 5,591,478 A    1/1997   Tokunaga et al.

FOREIGN PATENT DOCUMENTS

| | | |
|---|---|---|
| JP | 56-154967 | 11/1981 |
| JP | 60-149596 | 8/1985 |

(Continued)

OTHER PUBLICATIONS

Yun, J. W. and Song, S. K., "The Production of High-Content Fructo-oligosaccharides From Sucrose by the Mixed-Enzyme System of Fructosyltransferase and Glucose Oxidase," Biotechnology Letters, vol. 15, No. 6 (Jun. 1993) 573-576.*

(Continued)

*Primary Examiner* — Jeffrey Mornhinweg
(74) *Attorney, Agent, or Firm* — Wenderoth, Lind & Ponack, L.L.P.

(57) ABSTRACT

The invention is directed to a nystose crystal-containing powder that has excellent fluidity suitable for handling, and shows a suppressed powder-blown-up phenomenon. The nystose crystal-containing powder has a nystose content of 83 to 89 wt %; the powder has 0.2 to 18.6 wt % of gluconic acid relative to a total weight of nystose crystals contained in the powder; and the powder has a water content of 8 to 14 wt %.

12 Claims, 2 Drawing Sheets

(52) U.S. Cl.
CPC ............... *C12P 19/02* (2013.01); *C12P 19/14* (2013.01); *A23V 2002/00* (2013.01); *A61K 9/5015* (2013.01)

(58) Field of Classification Search
USPC ........................................................ 426/658
See application file for complete search history.

(56) References Cited

FOREIGN PATENT DOCUMENTS

| JP | 5-253407 | 10/1993 |
| --- | --- | --- |
| JP | 6-31160 | 2/1994 |
| JP | 6-165700 | 6/1994 |
| JP | 6-339388 | 12/1994 |
| JP | 8-173109 | 7/1996 |
| JP | 2010-273580 | 12/2010 |

OTHER PUBLICATIONS

Matsumoto, H., Tokunaga, T. and Hirayama, M., "Effect of Dehydrated Nystose Addition on the Reduction of Water Activity," Food Sci. Technol. Res., 7(1):94-98 (2001).*

Office Action dated Nov. 26, 2015 in corresponding Taiwanese patent application No. 102141032.
Jong Won Yun et al., "Batch Production of High-Content Fructo-Oligosaccharides from Sucrose by the Mixed-Enzyme System of β-Fructofuranosidase and Glucose Oxidase", Journal of Fermentation and Bioengineering, vol. 77, No. 2, pp. 159-163, 1994 (with English translation).
Office Action dated Apr. 19, 2016 in Chinese patent application No. 201380058767.3 (with English translation).
Hitoshi Matsumoto et al. "Effect of dehydrated nystose addition on the reduction of water activity", Food. Sci. Technol. Res., 7(1), pp. 94-98 (published on Jan. 30, 2007).
English translation of International Preliminary Report on Patentability and Written Opinion dated May 21, 2015 in PCT/JP2013/080533.
International Search Report dated Feb. 25, 2014 in International (PCT) Application No. PCT/JP2013/080533.
M. Novak et al., "Formation of Oligofructosides During Gluconate Production by *Aspergillus Niger*", Biotechnology Letters, vol. 18, No. 2, pp. 211-212, Feb. 1996.
G. A. Jeffrey et al., "The Tetrasaccharide Nytose Trihydrate: Crystal Structure Analysis and Hydrogen Bonding", Carbohydrate Research, vol. 247, pp. 37-50, 1993.
Extended European Search Report dated Apr. 6, 2016 in corresponding European Application No. 13852668.6.

\* cited by examiner

NYSTOSE CRYSTAL-CONTAINING POWDER

CROSS-REFERENCE TO RELATED APPLICATIONS

This application is based upon and claims the benefit of priority from Japanese Patent Application No. 2012-248358 filed on Nov. 12, 2012 and Japanese Patent Application No. 2013-177814 filed on Aug. 29, 2013; the entire contents of which are incorporated herein by reference.

BACKGROUND OF THE INVENTION

Field of the Invention

The present invention relates to a nystose crystal-containing powder which has fluidity suitable for handling and shows a suppressed powder-blown-up phenomenon, and to a method for producing the same.

Background Art

Nystose is a tetrasaccharide where two molecules of fructose are bound to sucrose. Nystose is one of components contained in fructooligosaccharides.

Nystose has useful properties such as a property of hardly causing tooth decay, a property to be selectively assimilated by intestinal bacteria, and the like. Furthermore, because nystose has strong moisture-absorbing ability, it can be used as a food desiccant (Patent Document 1).

Usefulness of nystose such as these has attracted attention and, so far, there have been made studies on methods for producing nystose crystals with an object to obtain highly pure nystose crystals (Patent Documents 2 to 4). According to these methods, there are obtained highly pure nystose crystals having nystose purity of 95 to 99%.

PRIOR ART DOCUMENTS

Patent Document

Patent Document 1: Japanese Patent Application Publication No. H06-31160
Patent Document 2: Japanese Patent Application Publication No. H06-165700
Patent Document 3: Japanese Patent Application Publication No. H06-339388
Patent Document 4: Japanese Patent Application Publication No. H05-253407

SUMMARY OF THE INVENTION

The nystose crystals of high purity which are obtained by conventional methods are generally in a form of fine powder having excellent fluidity. However, the conventional nystose crystals of high purity generate a powder-blown-up phenomenon only by carrying out a common operation such as weighing and the like and, thus, precautions become necessary when handling them. In order to maintain cleanliness of a working area, the powder-blown-up phenomenon is desired to be suppressed as much as possible. Ordinarily, in order to suppress the powder-blown-up phenomenon, fabrication of the powder into a granular form is performed by granulation. In order to perform such fabrication, a device for granulation processing becomes necessary. However, when it is intended to produce nystose crystals at a cost as low as possible to supply them to the market, a production method is desired which does not require introduction of a new device or process.

Therefore, the present inventors attempted to suppress occurrence of the powder-blown-up phenomenon of the highly pure nystose crystals by supplying water thereto under a high humidity condition. However, when the conventional nystose crystals of high purity were made to absorb water under a condition of relative humidity of 80% at 30° C., occurrence of the powder-blown-up phenomenon could not be suppressed.

The objects of the present invention are to provide a nystose crystal-containing powder which has fluidity suitable for handling and suppress occurrence of a powder-blown-up phenomenon, and to provide a method for producing the same.

In such a technical background, the present inventors found that a nystose crystal-containing powder, which has nystose purity (a nystose content) of a specific range, and which further contains a slight amount of gluconic acid and has a specific water content, has suitable fluidity and a property of suppressing the powder-blown-up phenomenon. The present invention is based on this finding.

According to the present invention, the following inventions are provided:

(1) a nystose crystal-containing powder, wherein: the powder has a nystose content of 71 to 90 wt %; the powder contains 0.2 to 18.6 wt % of gluconic acid relative to a total weight of nystose crystals contained in the powder; and the powder has a water content of 7 to 14 wt %;
(2) the nystose crystal-containing powder according to (1), wherein the powder has a melting point of 128 to 150° C.;
(3) the nystose crystal-containing powder according to (1) or (2), wherein the powder has a dispersion degree of 10 to 21%;
(4) the nystose crystal-containing powder according to any one of (1) to (3), wherein the powder has a nystose content of 83 to 89 wt %;
(5) the nystose crystal-containing powder according to any one of (1) to (4), wherein the powder contains 0.26 to 1.0 wt % of gluconic acid relative to the total weight of the nystose crystals;
(6) the nystose crystal-containing powder according to any one of (1) to (5), wherein the powder has a water content of 8 to 14 wt %;
(7) a method for producing a nystose crystal-containing powder, comprising the steps of:
(A) generating nystose by reacting sucrose with an enzyme solution containing β-fructofuranosidase and glucose oxidase;
(B) converting glucose in the reaction mixture solution into gluconic acid by glucose oxidase;
(C) adjusting a gluconic acid content in the solution obtained by steps (A) and (B) to 0.1 to 20 wt %;
(D) obtaining nystose crystals from the solution obtained by step (C); and
(E) adjusting a water content of the nystose crystals obtained by step (D),
(8) the method according to (7), wherein a nystose content is 55 wt % or more and a fructosyl-nystose content is less than 12 wt % in the solution obtained by step (C);
(9) the method according to (7) or (8), wherein the adjustment of the gluconic acid content in step (C) is performed by electrodialysis;
(10) the method according to any one of (7) to (9), further comprising, in step (B), a step of removing hydrogen peroxide, produced as a byproduct, by catalase;
(11) a nystose crystal-containing powder produced by the method according to any one of (7) to (10).

According to the present invention, the nystose crystal-containing powder can be provided having fluidity suitable for handling and showing a suppressed powder-blown-up phenomenon. The nystose crystal-containing powder of the present invention has improved handleability and, therefore, can be used suitably for products including various foods and drinks, medicaments, and the like. The nystose crystal-containing powder of the present invention can provide processed products with useful properties such as a property of hardly causing tooth decay, a property to be selectively assimilated by intestinal bacteria, and the like. Furthermore, the nystose crystal-containing powder of the present invention can be produced by a simple method of performing a moisture adjustment in an aging step without using a special granulating device for a purpose of suppressing occurrence of the powder-blown-up phenomenon.

DETAILED DESCRIPTION OF THE INVENTION

Figure 1:
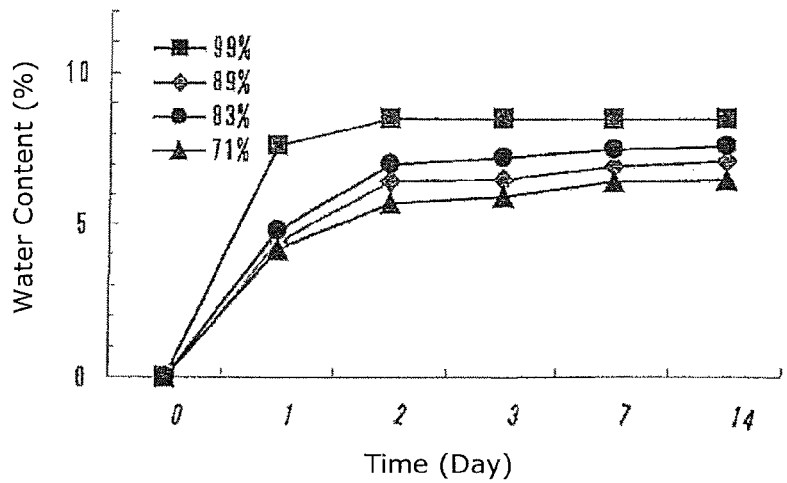
FIG. 1 is a graph related to step (E) of Example 1. The graph shows changes in the water contents of the nystose crystals (purity: 71 to 99%) when aged for 0 to 14 days under relative humidity of 20% at 30° C.

In the present invention, the term "nystose crystal-containing powder" means nystose crystals (in a powder form), the water content of which is adjusted.

The nystose crystal-containing powder of the present invention has a nystose content of 71 to 90 wt %, preferably 75 to 90 wt %, more preferably 75 to 89 w %, and even more preferably 83 to 89 wt %.

Here, the term "nystose content" is used interchangeably with the term "nystose purity" and means a weight ratio of nystose relative to a total weight of sugar (neutral sugar) other than gluconic acid contained in the nystose crystal-containing powder. The sugar (neutral sugar) other than gluconic acid includes, for example, fructose, glucose, sucrose, 1-kestose, nystose, and fructosyl-nystose. For example, the phrase "a nystose content of the nystose crystal-containing powder is 71 to 90 wt %" or the phrase "nystose purity of the nystose crystal-containing powder is 71 to 90 wt %" means that a proportion of nystose relative to the total weight of sugar other than gluconic acid is 71 to 90 wt % in the nystose crystal-containing powder. The nystose content of the nystose crystal-containing powder can be measured by a heretofore known method based on a sugar composition of the nystose crystals.

The nystose crystal-containing powder of the present invention has a water content of 7 to 14 wt %, preferably 8 to 14 wt %, more preferably 8 to 12 wt %, and even more preferably 9 to 12 wt %. Alternatively, the water content may be set to 8 to 10 wt %. The water content in the nystose crystal-containing powder can be measured in accordance with a general food analysis method, for example, a heating/drying method.

The nystose crystal-containing powder of the present invention can contain gluconic acid in an amount of 0.2 wt % or more relative to a total weight of nystose crystals but, from the viewpoint of taste, the amount is preferably 0.2 to 18.6 wt %, more preferably 0.26 to 4.2 wt %, even more preferably 0.26 to 1.0 wt %, and further even more preferably 0.26 to 0.48 wt %. Alternatively, the nystose crystal-containing powder may contain 0.2 to 0.5 wt % of gluconic acid. The content of gluconic acid in the nystose crystals can be measured in accordance with a heretofore known method. A measuring kit is also commercially available, and the gluconic acid content can be measured by a measuring kit such as, for example, "Food Analysis Reagent F-Kit D-Gluconic Acid/Gluconolactone (produced by J. K. International, Inc.)" and the like. In addition, when the content of gluconic acid contained in the nystose crystals exceeds 4.2 wt %, the nystose crystal-containing powder gives a salty taste as well as a sweet taste. Furthermore, when the gluconic acid content is 18.6 wt %, the nystose crystal-containing powder is more salty than sweet.

The melting point of the nystose crystal-containing powder of the present invention is 122 to 150° C., preferably 128 to 150° C., and more preferably 128 to 138° C. The melting point can be measured in accordance with a heretofore known method (for example, a clear melting point method). In Patent Document 1, there is disclosed a crystalline nystose hydrate having a nystose content of 83%, a water content of 6.2%, and a melting point of 120 to 124° C. Among the nystose crystal-containing powder of the present invention, one having a nystose content of 83% shows a melting point of 128 to 136° C., which is, therefore, different from the crystalline nystose hydrate of Patent Document 1.

The dispersion degree of the nystose crystal-containing powder of the present invention is preferably 10 to 21% and more preferably 12 to 21%. Here, the term "dispersion degree" is an index which shows easiness of the powder to scatter, and means that the larger the value is, the more easily the powder shows a powder-blown-up phenomenon. Generally, the dispersion degree is regarded as one of the factors related to a flashing property of powder. For example, when the dispersion degree exceeds 50%, the flashing property of the powder is considered to be high, and therefore special measures are thought to be necessary against generation of dust.

The dispersion degree is measured by a method such as the following. A predetermined weight (W) of a sample is allowed to drop from a predetermined height on a receiving pan, and a weight (W1) of the sample which accumulated on the receiving pan is measured. Furthermore, the dispersion degree is calculated according to the following formula:

$$\text{dispersion degree}(\%) = (W - W1)/W1 \times 100.$$

A specific method for measuring the dispersion degree of the nystose crystal-containing powder of the present invention includes a measurement method where 10 g of sample powder is weighed and the dispersion degree thereof is measured by a powder characteristics evaluation apparatus (for example, product name: Powder Tester, manufactured by Hosokawa Micron Corporation).

Preferably, the nystose crystal-containing powder of the present invention has a lower "dispersion degree," which indicates easiness of the powder to cause a powder-blown-up phenomenon, compared to the conventional high-purity nystose crystals and, on the other hand, has "fluidity," which indicates easiness of the powder to flow, in a proper state. As a method for evaluating fluidity, there are generally known a plurality of methods. Evaluation of fluidity of the nystose crystal-containing powder of the present invention can be performed by observation of appearance of the powder.

In the "observation of appearance of the powder," ease of flow is evaluated when the powder is transferred from a container storing the same to another container belonging to a measuring device and the like. The crystal-containing powder of the present invention is in a form of either good flowable powder or loosely coagulated fine granules and, therefore, has fluidity which allows preferable handling.

The nystose crystal-containing powder of the present invention can be produced by a method comprising the steps of:
(A) generating nystose by reacting sucrose with an enzyme solution containing β-fructofuranosidase and glucose oxidase;
(B) converting glucose in the reaction mixture solution into gluconic acid by glucose oxidase;
(C) adjusting a gluconic acid content in the solution obtained by steps (A) and (B) to 0.1 to 20 wt %;
(D) obtaining nystose crystals from the solution obtained by step (C); and
(E) adjusting a water content of the nystose crystals obtained by step (D).

In the following, each step will be described specifically.

Step A

In step (A), nystose can be generated by contacting sucrose with β-fructofuranosidase in an enzyme solution containing β-fructofuranosidase and glucose oxidase.

The enzyme solution can be prepared by mixing desired enzymes and a solvent. The solvent is not particularly limited but includes, for example, water, a buffer solution, and the like, among which preferable is water (an aqueous solution). A concentration of the enzymes in the enzyme solution suffices if it is an amount sufficient to make a target enzymatic reaction proceed. For example, the enzyme concentration can be adjusted so that β-fructofuranosidase is present in an amount equivalent to 1 to 30 U (especially, 2 to 15 U) relative to 1 g of sucrose, and glucose oxidase is present in an amount equivalent to 1 U or more (especially, 4 U or more (for example, 4 to 50 U)) relative to 1 g of sucrose. Further, when catalase is used, the concentration of the enzymes in the enzyme solution can be adjusted so that catalase is present in an amount equivalent to 10 U or more, especially, 100 U or more (for example, 100 to 200 U) relative to 1 g of sucrose.

In the method of the present invention, β-fructofuranosidase to be used can be one which has fructose transferring activity such that, when it is brought in contact with sucrose, a conversion rate of sucrose into nystose becomes 40% or more. The origin of the β-fructofuranosidase to be used is not particularly limited, but includes *Aspergillus, Penicillium,* or *Scopulariopsis*. β-Fructofuranosidase is preferably one derived from *Aspergillus niger* or *Aspergillus japonicus*, and more preferably one derived from the ATCC 20611 strain.

In the method of the present invention, β-fructofuranosidase and sucrose are contacted in a solution. Conditions therefor are not particularly limited as long as β-fructofuranosidase is in a state such that it can act on sucrose. A specific example is as follows. A concentration of sucrose in the reaction mixture solution may be selected suitably considering specific activity of the enzyme, reaction temperature, and the like, as long as it is in a range where sucrose is soluble. For example, the sucrose concentration is preferably in a range of 5 to 80 wt %, and more preferably is in a range of 30 to 70 wt %. From the viewpoint of an amount of dissolved oxygen in the reaction mixture solution, which will be described later, the sucrose concentration can be set more preferably in a range of 30 to 60 wt %, and even more preferably in a range of 30 to 40 wt %. The temperature and pH in the reaction of sucrose and β-fructofuranosidase are preferably in a range of optimum conditions for β-fructofuranosidase. For example, the reaction is carried out preferably under conditions of a temperature of about 20 to 70° C. and a pH of about 4 to 10, and more preferably in ranges of 25 to 40° C. and pH 5 to 8, respectively. An amount of addition of β-fructofuranosidase suffices if sucrose in the enzymatic reaction mixture solution can be utilized sufficiently. The reaction time can be changed suitably until an amount of nystose generated reaches maximum.

Meanwhile, in the method of the present invention, there is further mixed glucose oxidase in the reaction system and, therefore, these conditions can further be changed suitably depending on glucose oxidase to be used. Glucose oxidase will be described later.

Step (B)

In step (B), nystose is generated by contact of β-fructofuranosidase with sucrose and, at the same time, glucose which is produced as a byproduct can be converted to gluconic acid by glucose oxidase.

In the method of the present invention, simultaneously with a reaction to generate nystose by making β-fructofuranosidase act on sucrose, there is carried out a reaction to convert glucose, produced as a byproduct, to gluconic acid by glucose oxidase.

As glucose oxidase to be used for the method of the present invention, there can be used, for example, glucose oxidase derived from *Aspergillus niger*, or one derived from *Penicillium chrysogenum* or the like. Commercially available glucose oxidase preparations sometimes have invertase activity as sub-activity. Among enzyme preparations containing invertase, there are some which exhibit strong activity to hydrolyze generated nystose. Therefore, in glucose oxidase used in the present invention, it is desirable that the invertase activity which hydrolyzes nystose is weak, or there is no invertase activity contained.

An amount of glucose oxidase to be added suffices if it is sufficient to convert glucose produced as a byproduct. Further, because conversion from glucose to gluconic acid by glucose oxitase is an oxidation reaction, oxygen is necessary for the reaction. For this reason, in a conversion reaction of glucose to gluconic acid, it is desirable to stir the reaction mixture solution at a high speed while passing air therein in order to increase an amount of dissolved oxygen in the reaction mixture solution. A concentration of the dissolved oxygen can be increased by adjusting the concentration of the raw material sucrose or the reaction temperature. That is, the concentration of the dissolved oxygen in the reaction mixture solution can be increased by adjusting the concentration of the raw material sucrose to 60% or less, and preferably to 40% or less.

With regard to the reaction temperature, it is preferably set to 20° C. to 40° C. because the concentration of the dissolved oxygen decreases as the temperature increases. Further, when glucose is converted to gluconic acid, pH of the reaction mixture solution decreases because of gluconic acid. When the pH of the reaction mixture solution decreases, there occurs termination of the reaction to convert sucrose to nystose, acid hydrolysis of the generated nystose, or the like. Therefore, it is desirable to adjust the pH to near neutrality by adding a neutralizing agent suitably to the reaction mixture solution. The neutralizing agent which can be used includes sodium carbonate, calcium carbonate, calcium hydroxide, sodium hydroxide, potassium hydroxide, aqueous ammonia, and the like.

In the reaction to convert glucose into gluconic acid by glucose oxidase, hydrogen peroxide is produced as a byproduct. Because there are cases where oxidizing action of hydrogen peroxide deactivates the enzymes, it is desirable, if necessary, to add catalase which decomposes hydrogen peroxide.

Therefore, the method of the present invention further includes, in step (B) of converting glucose into gluconic acid by glucose oxidase, a method of removing hydrogen peroxide produced as a byproduct by catalase. As the catalase to be used, preferable is one derived from *Aspergillus niger*, *Micrococcus lysodeikticus*, or the like. Furthermore, the method also includes, in addition to a combined use of a glucose oxidase preparation and a catalase preparation, selecting and using a commercial glucose oxidase preparation which has catalase activity as sub-activity.

An amount of catalase to be added suffices if it is sufficient to convert hydrogen peroxide, produced as a byproduct, into oxygen and water. The reaction temperature and pH for catalase may be selected suitably as long as the conditions are such that the reaction to generate nystose and the reaction to convert glucose into gluconic acid by glucose oxidase proceed.

Step (B) is initiated when, in step (A), glucose is produced as a byproduct at the same time with generation of nystose.

Step (A) proceeds even when step (B) is initiated. That is, step (A) and step (B) proceed simultaneously.

Step (C)

In step (C), a content of gluconic acid in the solution obtained by steps (A) and (B) is adjusted to 0.1 to 20 wt %.

The method of the present invention includes a step of adjusting the gluconic acid content in the nystose-containing solution generated by steps (A) and (B) to 0.1 to 20 wt %. According to a study of the present inventors, when the gluconic acid content is not adjusted after step (B), the content of gluconic acid contained in the nystose-containing solution was about 40 wt %. In this case, nystose crystals could not be obtained (Example 7). Furthermore, in a solution after the gluconic acid content is adjusted, a recovery rate of crystals decreased by about 10 percentage points when the gluconic acid content was 20 wt % than when the gluconic acid content was 10 wt % (Example 7). Therefore, in the method of the present invention, it is desirable to adjust the concentration of gluconic acid in the nystose-containing solution to a suitable range. The concentration range includes preferably 20 wt % or less, more preferably 0.1 to 20 wt %, more preferably 0.1 to 10 wt %, more preferably 0.1 to 5 wt %, more preferably 0.1 to 2 wt %, and especially preferably 0.1 to 1 wt %.

As a method for adjusting the gluconic acid content in the nystose-containing solution, any method can be used as long as it allows selective removal of gluconic acid from the solution. Specifically, there may be mentioned electrodialysis, anion exchange chromatography, a method of precipitating and removing gluconic acid as a calcium salt, and the like. As the method for adjusting the gluconic acid content in the nystose-containing solution, it is desirable to use electrodialysis from the viewpoint of less loss of nystose during the step.

Further, in the method of the present invention, the nystose content in a sugar composition in the nystose-containing solution, after adjustment of the gluconic acid content, is preferably 55 wt % or more (for example, 55 to 100 wt %), and more preferably 60 wt % or more (for example, 60 to 100 wt %). Here, the term "nystose content" means a proportion (weight ratio) of nystose in the sugar composition of neutral sugars contained in the nystose-containing solution. The neutral sugars constituting the "sugar composition" specifically include fructose, glucose, sucrose, 1-kestose, nystose, and fructosyl-nystose. Further, a fructosyl-nystose content in the sugar composition in the solution after adjustment of the gluconic acid content is preferably less than 12 wt %, and more preferably 11 wt % or less (for example, 0 to 11 wt % or 0 to 10.2 wt %). Here, the term "fructosyl-nystose content" means a proportion (weight ratio) of fructosyl-nystose in the sugar composition of neutral sugars except gluconic acid in the solution. Therefore, as a preferable embodiment of the method of the present invention, the nystose content in the sugar composition in the solution after adjustment of the gluconic acid content is preferably 55 wt % or more, and more preferably 60 wt % or more, and the fructosyl-nystose content is preferably less than 12 wt %, and more preferably 11 wt % or less. The nystose content and the fructosyl-nystose content may be further adjusted considering the sugar composition in the nystose-containing solution after adjustment of the gluconic acid content. Meanwhile, it may be said to be technical common knowledge in the industry that, in the solution after adjustment of the gluconic acid content, the higher the nystose content is, or the lower the fructosyl-nystose content is, the more efficiently the nystose crystals can be obtained.

Step (D)

In step (D), the nystose crystals can be obtained from the solution obtained in step (C).

As a method for obtaining the nystose crystals from the solution obtained by step (C), there may be used a heretofore known method. For example, there may be employed a method described in Patent Document 3 and Patent Document 4. Specifically, the specific method is as follows. A sugar solution is concentrated so that a solid content thereof becomes 60 wt % or more, preferably 70 wt % or more by a concentration apparatus such as an evaporator and the like. To a concentrated solution obtained, nystose crystals are added as seed crystals, and thereafter the solution is stirred to disperse the crystals uniformly. The sugar solution obtained is allowed to stand to precipitate crystals. By subjecting a crystalline mixture after standing to solid-liquid separation, there can be obtained nystose crystals. A means of solid-liquid separation is not particularly limited, but includes an upper discharge centrifuge, a bottom discharge centrifuge, a filter press, a rotary drum filter (Oliver filter), a screw press, a belt press, and the like. In the method of the present invention, it is preferable to use the upper discharge centrifuge or the bottom discharge centrifuge.

In the above-described operation, viscosity of the solution before the solid-liquid separation can be adjusted by addition of deionized water before the solid-liquid separation operation, adjustment of the solution temperature, or the like. By adjusting the viscosity as above, the content of nystose in the finally obtainable crystal-containing powder can be adjusted suitably.

Step (E)

In step (E), the water content of the nystose crystals obtained by step (D) is adjusted.

Step (E) is a step of adjusting the water content of the nystose crystals obtained by step (D). A method of adjusting the water content is not particularly limited, but it is desirable to age the crystals under a specific humidity condition.

In the present invention, the term "aging" means an operation of placing the nystose crystals under a certain condition to let the crystals contain a predetermined amount of water. The condition for aging includes, at 30° C., a relative humidity condition of preferably 40 to 80%, more preferably 40 to 60%, and even more preferably 40 to 50%. The target water content of the nystose crystal-containing powder is preferably 7 to 14 wt %, more preferably 8 to 14 wt %, even more preferably 8 to 12 wt %, and further even more preferably 9 to 12 wt %. The aging time may be a time necessary for the nystose crystal-containing powder to reach the above-mentioned water content, but is usually about 1 day to 1 week. The aging temperature is set usually at around a room temperature, preferably at 20 to 35° C., and more preferably at 30° C.

The nystose crystal-containing powder of the present invention can be applied to heretofore known beverages, foods, and medicaments. The nystose crystal-containing powder of the present invention shows suppressed occurrence of the powder-blown-up phenomenon at the time of weighing and, therefore, is easy to handle when processing the powder. Accordingly, the nystose crystal-containing powder of the present invention is advantageous for use in industrial production.

According to a preferable embodiment of the present invention, a nystose crystal-containing powder is provided, wherein:

the powder has a nystose content of 83 to 89 wt %;
the powder contains 0.2 to 18.6 wt % of gluconic acid relative to a total weight of nystose crystals contained in the powder; and
the powder has a water content of 8 to 14 wt %.

According to a more preferable embodiment of the present invention, a nystose crystal-containing powder is provided, wherein:

the powder has a nystose content of 83 to 89 wt %;
the powder contains 0.2 to 1.0 wt % of gluconic acid relative to a total weight of nystose crystals contained in the powder; and
the powder has a water content of 8 to 14 wt %.

According to an even more preferable embodiment of the present invention, a nystose crystal-containing powder is provided, wherein:

the powder has a nystose content of 83 to 89 wt %;
the powder contains 0.26 to 1.0 wt % of gluconic acid relative to a total weight of nystose crystals contained in the powder; and
the powder has a water content of 8 to 14 wt %.

According to a further even more preferable embodiment of the present invention, a nystose crystal-containing powder is provided, wherein:

the powder has a nystose content of 83 to 89 wt %;
the powder contains 0.26 to 1.0 wt % of gluconic acid relative to a total weight of nystose crystals contained in the powder; and
the powder has a water content of 8 to 12 wt %.

According to a preferable embodiment of the present invention, a method for producing a nystose crystal-containing powder is provided, comprising the steps of:
(A) generating nystose by reacting sucrose with an enzyme solution containing β-fructofuranosidase, glucose oxidase, and catalase;
(B1) converting glucose in the reaction mixture solution into gluconic acid by glucose oxidase;
(B2) removing hydrogen peroxide in the reaction mixture solution by catalase;
(C) adjusting a gluconic acid content in the solution obtained by steps (A) and (B) to 0.1 to 20 wt % (here, a nystose content in the solution is 55 wt % or more and a content of fructosyl-nystose is less than 12 wt %);
(D) obtaining nystose crystals from the solution obtained by step (C); and
(E) adjusting a water content of the nystose crystals obtained by step (D).

According to a more preferable embodiment of the present invention, a method for producing a nystose crystal-containing powder is provided, comprising the steps of:
(A) generating nystose by reacting sucrose with an enzyme solution containing β-fructofuranosidase, glucose oxidase, and catalase;
(B1) converting glucose in the reaction mixture solution into gluconic acid by glucose oxidase;
(B2) removing hydrogen peroxide in the reaction mixture solution by catalase;
(C) adjusting a gluconic acid content in the solution obtained by steps (A) and (B) to 0.1 to 20 wt % (here, a nystose content in the solution is 55 wt % or more and a content of fructosyl-nystose is less than 12 wt %);
(D) obtaining nystose crystals having a nystose content of 83 to 89 wt % from the solution obtained by step (C); and
(E) adjusting a water content of the nystose crystals obtained by step (D) to obtain a nystose crystal-containing powder having a water content of 8 to 14 wt %.

According to the present invention, the following inventions are also provided:
(1) a nystose crystal powder, wherein (a) the powder has a nystose purity of 75 to 90%, (b) the powder contains 0.2 to 0.5 wt % of gluconic acid, and (c) the powder has a water content of 8 to 14 wt %;
(2) the nystose crystal powder according to (1), wherein (d) the powder has a melting point of 128 to 150° C.;
(3) the nystose crystal powder according to (1) or (2), wherein (e) the powder has a dispersion degree of 10 to 21%;
(4) the nystose crystal powder according to any one of (1) to (3), wherein (a) the powder has a nystose purity of 83 to 89%;
(5) the nystose crystal powder according to any one of (1) to (4), wherein (b) the powder contains 0.26 to 0.48 wt % of gluconic acid;
(6) the nystose crystal powder according to any one of (1) to (5), wherein (c) the powder has a water content of 9 to 12 wt %;
(7) a method for producing a nystose crystal powder, comprising the steps of:
(A) generating nystose by reacting sucrose with an enzyme solution containing β-fructofuranosidase;
(B) converting glucose in the reaction mixture solution into gluconic acid by making glucose oxidase act on glucose simultaneously with the reaction in the step (A);
(C) adjusting a gluconic acid content in the reaction mixture solution to 0.1 to 1 wt %, subsequently to the step (B);
(D) obtaining nystose crystals from the solution obtained by the step (C); and
(E) adjusting a water content of the nystose crystals obtained by the step (D).
(8) the method according to (7), wherein a nystose content is 55% or more and a fructosyl-nystose content is 11% or less in a sugar composition in the solution obtained by step (C);
(9) the method according to (7) or (8), wherein, in step (C), a method of adjusting the gluconic acid content is electrodialysis;

(10) the method according to any one of (7) to (9), further including, in step (B), removing hydrogen peroxide, produced as a byproduct, by catalase;
(11) a nystose crystal powder produced by the method according to any one of (7) to (10).

According to the present invention, the following inventions are also further provided:
(1) a nystose crystal powder, wherein (a) the powder has a nystose purity of 71 to 90%, (b) the powder contains 0.2 to 18.6 wt % of gluconic acid, and (c) the powder has a water content of 7 to 14 wt %;
(2) the nystose crystal powder according to (1), wherein (d) the powder has a melting point of 128 to 150° C.;
(3) the nystose crystal powder according to (1) or (2), wherein (e) the powder has a dispersion degree of 10 to 21%;
(4) the nystose crystal powder according to any one of (1) to (3), wherein (a) the powder has a nystose purity of 83 to 89 wt %;
(5) the nystose crystal powder according to any one of (1) to (4), wherein (b) the powder contains 0.26 to 1.0 wt % of gluconic acid;
(6) the nystose crystal powder according to any one of (1) to (5), wherein the powder has a water content of 9 to 12 wt %;
(7) a method for producing a nystose crystal powder, comprising the steps of:
(A) generating nystose by reacting sucrose with an enzyme solution containing β-fructofuranosidase;
(B) converting glucose in the reaction mixture solution into gluconic acid by making glucose oxidase act on glucose simultaneously with the step (A);
(C) adjusting a gluconic acid content in the reaction mixture solution to 0.1 to 20 wt %, subsequently to the steps (A) and (B);
(D) obtaining nystose crystals from the solution obtained by the steps (A) to (C); and
(E) adjusting a water content of the nystose crystals obtained in the step (D).
(8) the method according to (7), wherein a nystose content is 55% or more and a fructosyl-nystose content is 11% or less in a sugar composition in the solution obtained by steps (A) to (C);
(9) the method according to (7) or (8), wherein, in step (C), a method of adjusting the gluconic acid content is electrodialysis;
(10) the method according to any one of (7) to (9), further including, in step (B), removing hydrogen peroxide, produced as a byproduct, by catalase;
(11) a nystose crystal-containing powder produced by the method according to any one of (7) to (10).

EXAMPLES

The present invention will be described in detail with reference to the following Examples, but the present invention is not limited to these Examples.

Reference Example 1: Preparation of β-Fructofuranosidase

A medium of 350 mL containing 2.0% of bouillon powder, 5.0% of sucrose, and 0.5% of CMC was added to a conical flask. After sterilization, *Aspergillus japonicus* ATCC 20611 strain was inoculated thereon and cultured at 28° C. for 20 hours to prepare a seed culture liquid. To a 30 L jar fermenter, there was added a 15 L medium containing 5.0% of sucrose, 3.6% of a yeast extract, and 0.5% of CMC. After adjusting pH to 6.5, the medium was sterilized at 120° C. for 30 minutes. Subsequently, 350 mL of the seed culture liquid was inoculated aseptically on the medium and cultured at 28° C. for 72 hours. After completion of culturing, the culture liquid was centrifuged and, further, freeze-dried to obtain crude enzyme-including microbial cell having fructose transfer activity. The fructose transfer activity of the crude enzyme-including microbial cell was 1,580 U/g (microbial cell weight). In addition, the fructose transfer activity is defined as follows: when 2.0 mL of a 25% sucrose solution, 1.0 mL of an enzyme solution, and 2.0 mL of McIlvaine's buffer solution (pH 5.0) are mixed and reacted at 40° C. for 60 minutes, an amount of enzyme which generates 1 μmol of GF2 per 1 minute is defined as 1 U (unit). The crude enzyme-including microbial cell were freeze-dried and used as β-fructofuranosidase in the subsequent tests.

Example 1: Production of Nystose Crystal-Containing Powder (1)

Step (A) and Step (B)

A substrate solution containing 30 wt % of sucrose was prepared by dissolving 578 g of sucrose in 1350 g of distilled water. The substrate solution was charged into a 3 L jar fermenter, and the following enzymes were added therein: 3,000 U of β-fructofuranosidase (Reference Example 1) and 3,000 U of glucose oxidase (product name: HYDERASE 15, produced by Amano Enzyme Inc.). Conditions of an enzymatic reaction were: temperature, 30° C.; pH, 7.0; stirring speed, 600 rpm; and air flow rate, 3 L/minute. Sampling was performed after 0, 2, 4, and 20 to 24 hours after initiation of the enzymatic reaction. The reaction was terminated by deactivating the enzyme by heating the reaction mixture solution after 24 hours from initiation of the reaction by a hot water bath set at 82° C. for 30 minutes. Further, to the solution after the reaction, activated charcoal was added in a proportion of 0.3% relative to the weight of the substrate. Successively, the solution was filtered by a filter paper and, thereafter, by a 0.45 μm filter.

Each of the obtained reaction mixture solutions was subjected to a sugar composition analysis. The sugar composition analysis was performed under the following conditions: column, RT 250-4.0 LiChrospher 100 NH2 (Cica-Reagent Co.); mobile phase, 66% acetonitrile; flow rate, 1 ml/min; column temperature, 40° C.; and detector, differential refractometer. One example of the results is shown in Table 1.

TABLE 1

| reaction time (hr) | fructose (%) | glucose (%) | sucrose (%) | 1-kestose (%) | nystose (%) | fructosyl-nystose (%) |
|---|---|---|---|---|---|---|
| 0 | 0.0 | 0.0 | 100.0 | 0.0 | 0.0 | 0.0 |
| 2 | 0.0 | 3.1 | 75.7 | 20.2 | 1.0 | 0.0 |
| 4 | 0.7 | 4.0 | 57.5 | 35.0 | 2.8 | 0.0 |
| 20 | 2.1 | 0.9 | 2.7 | 38.2 | 52.0 | 4.1 |
| 21 | 2.3 | 0.5 | 2.1 | 35.7 | 55.2 | 4.2 |
| 22 | 2.4 | 0.0 | 3.0 | 32.0 | 57.2 | 5.4 |
| 23 | 2.8 | 0.0 | 2.8 | 28.4 | 59.4 | 6.6 |
| 24 | 2.6 | 0.0 | 2.3 | 26.8 | 60.9 | 7.4 |
| after de-activation | 3.0 | 0.5 | 1.5 | 25.1 | 61.8 | 8.1 |

Table 1 shows that, when 20 hours had passed after initiation of the reaction, the nystose content in the reaction mixture solution increased to 50% or more. It also shows that, when 24 hours had passed from the initiation of the reaction, the nystose content increased to 60% or more.

Step (C)

The content of gluconic acid contained in the reaction mixture solution after filtration, obtained by the steps (A) and (B), was adjusted by electrodialysis.

The gluconic acid content was measured by using Food Analysis Reagent F-Kit D-Gluconic Acid/Gluconolactone (produced by J. K. International, Inc.).

Electrodialysis was performed under the following conditions: electrodialysis apparatus, MICRO ACILYZER S3 (manufactured by Astom Corporation); and cartridge, AC-220-550 (manufactured by Astom Corporation). Electrodialysis was performed for 7.5 hours by feeding the reaction mixture solution from a desalted liquid tank side of the electrodialysis apparatus and by feeding deionized water of the same amount as the reaction mixture solution from a concentrated liquid tank side. Sampling was performed at regular intervals immediately after electrodialysis was initiated. A desalted liquid after electrodialytic treatment was taken as a nystose-containing fraction, and a concentrated liquid after the treatment was taken as a gluconic acid-containing fraction. Each of the fractions was measured for a solid content concentration (Brix), pH, electric conductivity (EC), and a gluconic acid content (GA). The results are shown in Table 2.

TABLE 2

| dialysis time (hr) | nystose-containing fraction | | | | gluconic acid-containing fraction | | | |
|---|---|---|---|---|---|---|---|---|
| | Brix | pH | EC (mS/cm) | GA (w/v %) | Brix | pH | EC (mS/cm) | GA (w/v %) |
| 0 | 31.5 | 6.4 | 11.6 | 11.8 | 0 | 5.9 | 0.05 | 0 |
| 1 | 30.9 | 6.2 | 10.8 | 11.4 | 0.9 | 6.0 | 2.7 | 1.0 |
| 2 | 30.3 | 6.2 | 10.0 | 9.9 | 2.7 | 6.6 | 6.4 | 2.5 |
| 3 | 29.5 | 6.0 | 9.2 | 9.1 | 4.4 | 6.9 | 9.3 | 4.6 |
| 4 | 28.7 | 5.8 | 8.0 | 7.5 | 5.9 | 7.0 | 11.7 | 6.3 |
| 5 | 27.5 | 5.8 | 6.2 | 5.2 | 7.9 | 7.0 | 14.4 | 8.5 |
| 6 | 26.3 | 5.5 | 3.7 | 3.5 | 9.7 | 7.1 | 16.7 | 11.1 |
| 7 | 25.3 | 4.9 | 1.2 | 1.0 | 11.1 | 7.3 | 17.9 | 12.6 |
| 7.5 | 25.0 | 4.5 | 0.48 | 0.3 | 11.3 | 7.4 | 18.3 | 12.9 |

Table 2 shows that the electric conductivity and the gluconic acid content of the nystose-containing fraction decreased by performing electrodialysis. It also shows that the electric conductivity of the nystose-containing fraction was 1.2 mS/cm after 7 hours from initiation of the electrodialysis and was 0.48 mS/cm after 7.5 hours. Further, it shows that the content of gluconic acid contained in the nystose-containing fraction was 11% (W/V) or more when electrodialysis was initiated, whereas, after 7 hours from the initiation of electrodialysis, it decreased to 1.0% (W/V) after 7 hours and to 0.3% (W/V) after 7.5 hours from the initiation of the electrodialysis.

Furthermore, Table 2 shows that the pH of the nystose-containing fraction decreased from pH 6.4 before electrodialysis to as low as pH 4.5. In this example, considering that nystose is liable to be hydrolyzed at pH 5.0 or less, the nystose-containing fraction after electrodialysis was adjusted to pH 6.5 using a 1 M sodium hydroxide solution.

The nystose-containing fraction after 7.5 hours from the initiation of the electrodialysis was subjected to a sugar composition analysis. The results are shown in Table 3.

TABLE 3

| fructose (%) | glucose (%) | sucrose (%) | 1-kestose (%) | nystose (%) | fructosyl-nystose (%) |
|---|---|---|---|---|---|
| 2.8 | 0.4 | 2.4 | 25.4 | 60.1 | 8.9 |

Table 3 shows that the nystose content in the nystose-containing fraction after 7.5 hours from the initiation of the electrodialysis was 60% or more.

Step (D)

The nystose-containing fraction obtained by step (C) was concentrated by an evaporator until the solid content concentration became 76 wt %. To the concentrated solution, seed crystals (nystose crystals of 95% purity; crystals obtained in accordance with the method described in Example 1 of Japanese Patent Application Publication No. H06-311160) were added under stirring at 30 rpm. While continuing to stir at 30 rpm, the liquid temperature was decreased gradually from 55° C. to 30° C. over about 48 hours to allow crystals to precipitate.

After the above crystallization operation, separation of centrifugal syrup was performed using a small-sized centrifuge, and the crystals remaining on a filter cloth were dried under reduced pressure at 70° C. In order to adjust the crystal purity, the following operations were performed as a pre-treatment of the separation step:

(pretreatment a): before the separation step, temperature of the processing liquid after the crystallization operation was adjusted to 20° C. and, thereafter, deionized water was added to adjust the solid content concentration in the processing liquid to 56 wt %;

(pretreatment b): before the separation step, temperature of the processing liquid after the crystallization operation was adjusted to 55° C.; and (pretreatment c): before the separation step, temperature of the processing liquid after the crystallization operation was adjusted to 45° C.

The purity and gluconic acid content of the nystose crystals obtained are shown in Table 4. The gluconic acid content was measured using the commercially available kit in the same manner as in step (C).

TABLE 4

| | nystose purity (%) | gluconic acid content (wt %) |
|---|---|---|
| nystose crystals (pretreatment a) | 89 | 0.26 |
| nystose crystals (pretreatment b) | 83 | 0.48 |
| nystose crystals (pretreatment c) | 71 | 0.70 |

Table 4 shows that crystals having nystose purity of 71 to 89% were obtained by steps (A) to (D). Furthermore, it shows that the gluconic acid contents of the crystals were 0.2 to 0.7 wt %.

Step (E)

The nystose crystals (purity 71%, 83%, and 89%) obtained by the steps (A) to (D) and the nystose crystals described in the Patent Document 1 having a nystose content (purity) of 99% were pre-dried at 70° C. under reduced pressure for 24 hours and, thereafter, 1 g each of the crystals was weighed into a sample bottle which was pre-dried in the same manner, and a weight thereof on day 0 was measured. The samples were placed in sealed vessels adjusted to relative humidity of 20%, 40%, 60%, and 80% at 30° C., respectively, and were aged. The samples which were aged for 1, 2, 3, 7, and 14 days under the respective conditions were taken out and were weighed. The water contents were calculated as follows.

Water content(%)=(sample weight after aging−day 0 weight)/(day 0 weight)×100

With regard to changes in the water contents, results at relative humidity of 20%, 40%, 60%, and 80% are shown in FIG. 1, FIG. 2, FIG. 3, and FIG. 4, respectively.

Furthermore, each sample was evaluated, as fluidity, for easiness to flow when transferring the sample into another container according to the following criteria: 5, very good flowable fine powder; 4, good flowable powder; 3, loosely coagulated granules; 2, a state where lumps are formed; and 1, a deliquesced state. A state suitable for handling refers to the 5 to 3 above.

Furthermore, with regard to the samples in a state suitable for handling, the powder-blown-up phenomenon which occurs when transferring the sample into a container was evaluated as follows: ++, a powder-blown-up phenomenon occurs; +, a powder-blown-up phenomenon occurs slightly; −, no powder-blown-up phenomenon occurs.

Nystose Crystal-Containing Powder of 99% Purity

Under all aging conditions, the water content of the nystose crystal-containing powder of 99% purity from day 1 to day 14 showed nearly a constant value between 7.6 to 9.2 wt % (FIGS. 1 to 4). Further, in all samples under all aging conditions, the nystose crystal-containing powder was very good flowable fine powder but there occurred the powder-blown-up phenomenon (evaluation: 5, ++ to +).

Nystose Crystal-Containing Powder of 83% Purity and 89% Purity

When the nystose crystal-containing powder of 83% purity and 89% purity were aged under a relative humidity of 20% for 1 to 14 days, the water contents became 4.4 to 7.6 wt % (FIG. 1). The crystals were each very good flowable fine powder but there occurred the powder-blown-up phenomenon (evaluation: 5, ++).

Figure 2:
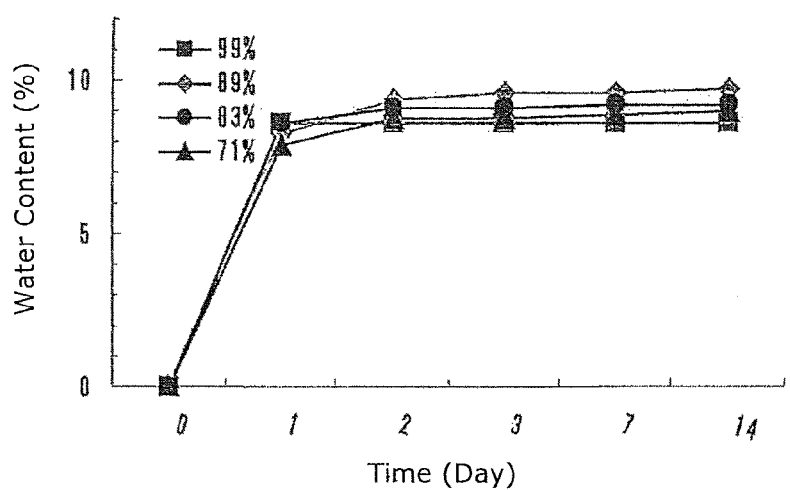
FIG. 2 is a graph related to step (E) of Example 1. The graph shows changes in the water contents of the nystose crystals (purity: 71 to 99%) when aged for 0 to 14 days under relative humidity of 40% at 30° C.

When the nystose crystal-containing powder of 83% purity and 89% purity were aged under relative humidity of 40%, the water contents became 8.3 to 8.6 wt. % on day 1 of aging (FIG. 2), and each was suppressed in occurrence of the powder-blown-up phenomenon while being very good flowable fine powder (evaluation: 5, −). On days 2 to 14 of aging, the water contents became 9.1 to 9.7 wt % (FIG. 2). Each sample was good flowable powder and was suppressed in occurrence of the powder-blown-up phenomenon (evaluation: 4, −). That is, the crystal-containing powder of nystose purity of 83% to 89%, which had been aged under relative humidity of 40% at 30° C., had fluidity suitable for handling and was suppressed in occurrence of the powder-blown-up phenomenon (evaluation: 4 to 5, −). The water contents of the crystal-containing powder were in a range of 8 to 10 wt %.

When aged under relative humidity of 60%, the crystal-containing powder of 89% nystose purity showed a nearly constant water content of 10.7 to 10.8 wt % on days 1 to 14 of aging (FIG. 3), each sample being good flowable powder and being suppressed in occurrence of the powder-blown-up phenomenon (evaluation: 4, −). Further, the crystal-containing powder of 83% nystose purity showed a nearly constant water content of 10.7 to 11.2 wt % on days 1 to 14 of aging (FIG. 3), each sample being loosely coagulated granules and being suppressed in occurrence of the powder-blown-up phenomenon (evaluation: 3, −). That is, the crystal-containing powder of nystose purity of 83% to 89%, aged under relative humidity of 60% at 30° C., had fluidity suitable for handling and was suppressed in occurrence of the powder-blown-up phenomenon (evaluation 3 to 4, −). The water contents of the crystal-containing powder were in a range of 10 to 12 wt %.

When aged under relative humidity of 80%, the crystal-containing powder of 89% nystose purity showed a water content of 11.1 to 11.8 wt % on days 1 to 3 of aging (FIG. 4), each sample being good flowable powder and being suppressed in occurrence of the powder-blown-up phenomenon (evaluation: 4, −). Further, on days 7 to 14 of aging, the water content was 11.9 to 12.0 wt % (FIG. 4), each sample being loosely coagulated granules and being suppressed in occurrence of the powder-blown-up phenomenon (evaluation: 3, −). Further, the crystal-containing powder of 83% nystose purity showed a water content of 11.1 to 13.6 wt % on days 1 to 14 of aging (FIG. 4), each sample being loosely coagulated granules and being suppressed in occurrence of the powder-blown-up phenomenon (evaluation: 3, −). That is, the crystal-containing powder of nystose purity of 83% to 89%, aged under relative humidity of 80% at 30° C., had fluidity suitable for handling and was suppressed in occurrence of the powder-blown-up phenomenon (evaluation 3 to 4, −). The water contents of the crystal-containing powder were in a range of 11 to 14 wt %.

Nystose Crystal-Containing Powder of 71% Purity

When the nystose crystal-containing powder of 71% purity was aged for 14 days under relative humidity of 20%, the water content became 4.2 to 6.5 wt % (FIG. 1). The crystals were all very good flowable fine powder, but the powder-blown-up phenomenon occurred (evaluation: 5, ++). Furthermore, when aged under a relative humidity of 40%, the water content became 7.9 to 9.0 wt % on days 1 to 14 of aging (FIG. 2), each being all good flowable powder and being suppressed in occurrence of the powder-blown-up phenomenon (evaluation: 4, −).

Figure 3:
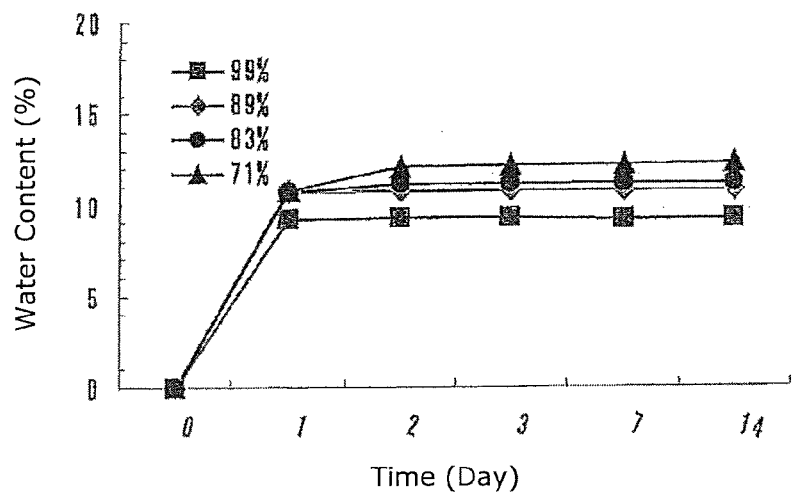
FIG. 3 is a graph related to step (E) of Example 1. The graph shows changes in the water contents of the nystose crystals (purity: 71 to 99%) when aged for 0 to 14 days under relative humidity of 60% at 30° C.
Figure 4:
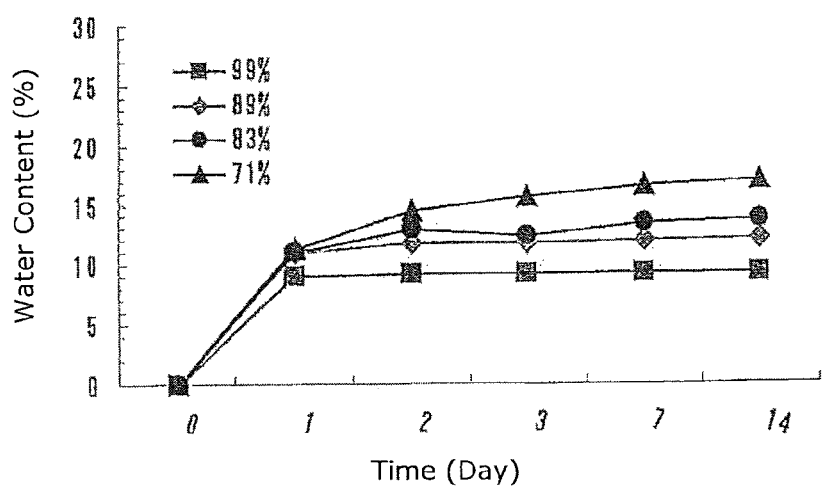
FIG. 4 is a graph related to step (E) of Example 1. The graph shows changes in the water contents of the nystose crystals (purity: 71 to 99%) when aged for 0 to 14 days under relative humidity of 80% at 30° C.

When the nystose crystal-containing powder of 71% purity was aged under relative humidity of 60% and 80% for 1 to 14 days, respectively, the water content of each became 10.8 to 12.3 wt % and 11.3 to 16.9 wt %, respectively (FIGS. 3 and 4). All samples under all aging conditions were in a state of lump formation (evaluation: 2).

From the results above, nystose crystal-containing powder having fluidity suitable for handling and being suppressed in occurrence of the powder-blown-up phenomenon could be obtained by aging, in step (E), crystal-containing powder of nystose purity of 71 to 89% under conditions of relative humidity of 40 to 80% (however, 50% or less in the case of nystose purity of 71%, also considering the results of Example 2) at 30° C. The water content of the crystal-containing powder was in a range of 7.9 to 14 wt %. From the results of step (D), the content of gluconic acid contained in the crystal-containing powder was in a range of 0.2 to 0.7 wt %.

In addition, among the ranges mentioned above, the nystose crystal-containing powder having especially favorable properties (evaluation of fluidity, 4 to 5; occurrence of powder-blown-up phenomenon, −) had such characteristics as nystose purity of 83 to 89%, a gluconic acid content in the nystose crystals 0.2 to 0.5 wt %, and a water content of 8 to 12 wt %. The crystal-containing powder was obtained by aging under relative humidity of 40 to 60% at 30° C. for 1 to 14 days.

Example 2: Measurement of Degree of Dispersion of Nystose Crystal-Containing Powder The degrees of dispersion were measured using crystal-containing powder of nystose purity of 71%, 83%, and 89% obtained in accordance with step (E) of Example 1, and nystose crystals of nystose contents (purity) of 95% and 99% described in Patent Document 1. Meanwhile, aging conditions were: day 0 (after preliminary drying); and relative humidity of 40% and 50% at 30° C. for 3 days.

The degree of dispersion was measured using a powder characteristics tester (product name: Powder Tester PT-E, manufactured by Hosokawa Micron Corporation). The prepared sample of 10 g (=W) was weighed into an uppermost part of a unit for measuring the degree of dispersion, and the sample was allowed to drop on a watch glass placed at a lower part. The degree of dispersion was determined according to the following calculation formula from the weight (=W1) of the sample which accumulated on the watch glass. The results are shown in Table 5. Further, evaluation of the powder-blown-up phenomenon of each sample was performed in the same way as in Example 1, and the results are shown in Table 5.

Degree of dispersion(%)=(W−W1)/W×100

TABLE 5

| aging condition | crystal purity (%) | | | | |
|---|---|---|---|---|---|
| (30° C.) | 99 | 95 | 89 | 83 | 71 |
| 0 day | 39.6% (++) | 39.4% (++) | 39.0% (++) | 39.4% (++) | 39.4% (++) |
| RH 40%, 3 days | 27.5% (++) | 27.8% (++) | 20.8% (−) | 12.5% (−) | 10.3% (−) |
| RH 50%, 3 days | 28.1% (++) | 28.6% (++) | 19.5% (−) | 17.6% (−) | 23.4% (−) |

With regard to the crystal-containing powder of nystose purity of 95% and 99%, the powder-blown-up phenomenon occurred in each test section. The degrees of dispersion were 27% or more in the test sections. On the other hand, the samples (water content: 8.8 to 12.2 wt %) obtained by aging the crystal-containing powder of nystose purity of 71 to 89% under relative humidity of 40 to 50% at 30° C. did not show the powder-blown-up phenomenon. The degrees of dispersion of the test sections were 10 to 25%. However, the sample obtained by aging the crystal-containing powder of nystose purity of 71% under relative humidity of 50% was in a state where lumps existed. Therefore, the degree of dispersion of the nystose crystal-containing powder being suppressed in occurrence of the powder-blown-up phenomenon was 10 to 21%. The nystose crystal-containing powder of nystose purity of 83 to 89%, which provided especially favorable characteristics in Example 1, showed the degrees of dispersion of 12 to 21%.

Example 3: Measurement of Melting Point of Nystose Crystal-Containing Powder Melting points were measured using samples (pre-dried materials) obtained by drying the crystal-containing powder of nystose purity of 71%, 83%, and 89%, obtained in Example 1, for 24 hours by a vacuum dryer set at 70° C. and using samples (aged materials) obtained by aging the same under relative humidity of 60% at 30° C. for 3 days (aged material). In addition, the crystal-containing powder of nystose purity of 85%, 80%, and 75% obtained by adjusting the pre-treatment temperatures in step (D) of Example 1 was aged in the same manner and subjected to melting point measurements. The measurements were outsourced to Japan Food Research Laboratories and performed by a clear melting point method. The results are shown in Table 6.

TABLE 6

| | nystose crystal purity (%) | | | | | |
|---|---|---|---|---|---|---|
| | 89 | 85 | 83 | 80 | 75 | 71 |
| pre-dried material | 140-150° C. | — | 136° C. | — | — | 135° C. |
| aged material | 138° C. | 128° C. | 128° C. | 129° C. | 128° C. | 122° C. |

Table 6 shows that the melting points of the crystal-containing powder of nystose purity of 75 to 89% were 128 to 150° C. It also shows that the melting points of the aged crystal-containing powder of nystose purity of 71 to 89% were 122 to 138° C. Further, it shows that the melting points of the aged crystal-containing powder of nystose purity of 83 to 89% were 128 to 138° C.

Example 4: Production of Nystose Crystal-Containing Powder (2): Study of Addition of Catalase in Step (B)

Step (A) and Step (B)

A substrate solution containing 30 wt % of sucrose was prepared by dissolving 578 g of sucrose in 1350 g of distilled water. The substrate solution was added to a 3 L jar fermenter and a reaction was initiated by addition of the following enzymes.

Added to all test sections: β-fructofuranosidase (Reference Example 1) 8,700 U.

Added to respective test sections: the following enzymes were added to respective test sections as glucose oxydase:
(1) HYDERASE 15 (produced by Amano Enzyme Inc.) 27,200 U;
(2) Maxazyme (produced by DSM Japan Co., Ltd.) 27,400 U;
(3) Bakezyme (produced by DSM Japan Co., Ltd.) 27,350 U;
(4) Sumizyme GOP (produced by Shin Nihon Chemical Co., Ltd.) 27,250 U; and
(5) Sumizyme PGO (produced by Shin Nihon Chemical Co., Ltd.) 27,250 U.

In addition, the enzyme unit (U) of glucose oxidase was measured as follows. By having the glucose oxidase act on glucose as a substrate, hydrogen peroxide was generated. In the presence of the generated hydrogen peroxide, 4-aminoantipyrine, and phenol, peroxidase was allowed to act, and a quinoimine dye generated was measured at a wavelength of 500 nm and was quantified. An amount of the enzyme which was necessary for oxidizing 1 μmol of glucose per minute under a condition of pH 7.0 was taken as 1 unit (U)

In test sections where no catalase was added, reactions were initiated by adding β-fructofuranosidase and one kind of the aforementioned glucose oxidase. In test sections where catalase was added, the following enzyme was added in addition to β-fructofuranosidase and one kind of the glucose oxidase: Leonet (produced by Nagase Chemtex Corporation) 100,000 U.

Conditions of the enzymatic reaction were set as follows: temperature, 30° C.; pH, 6.0; rate of stirring, 800 rpm; and air flow rate, 3 L/minute. Sampling was performed every hour for 8 hours from the initiation of the enzymatic reaction. Each reaction mixture solution obtained was subjected to a sugar composition analysis in accordance with the method described in Example 1. The results are shown in the following tables: Table 7, HYDELASE 15+catalase; Table 8, HYDELASE 15 (catalase not added); Table 9, Maxazyme+catalase; Table 10, Maxazyme (catalase not added); Table 11, Bakezyme+catalase; Table 12, Bakezyme (catalase not added); Table 13, Sumizyme GOP+catalase; Table 14, Sumizyme GOP (catalase not added); Table 15, Sumizyme PGO+catalase; and Table 16, Sumizyme PGO (catalase not added).

TABLE 7

| | HYDERASE 15 + catalase [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 0.8 | 1.2 | 1.6 | 2.2 | 2.8 | 3.2 | 4.0 | 4.0 |
| glucose (%) | 0.0 | 5.8 | 4.8 | 2.8 | 1.6 | 1.2 | 0.7 | 0.7 | 0.5 |
| sucrose (%) | 100.0 | 58.4 | 35.0 | 11.9 | 5.6 | 3.8 | 3.4 | 3.0 | 3.1 |
| 1-kestose (%) | 0.0 | 32.7 | 50.7 | 59.6 | 50.0 | 35.6 | 26.6 | 19.9 | 16.6 |
| nystose (%) | 0.0 | 2.4 | 8.3 | 24.2 | 37.8 | 50.3 | 57.1 | 59.1 | 58.8 |
| fructosyl-nystose (%) | 0.0 | 0.0 | 0.0 | 0.0 | 2.9 | 6.4 | 9.0 | 13.2 | 17.0 |

TABLE 8

| | HYDERASE 15 (catalase not added) [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 1.4 | 2.0 | 3.2 | 3.9 | 4.8 | 5.7 | 6.5 | 7.2 |
| glucose (%) | 0.0 | 7.2 | 5.7 | 3.5 | 2.0 | 1.5 | 1.0 | 0.9 | 0.0 |
| sucrose (%) | 100.0 | 52.3 | 29.2 | 10.6 | 5.5 | 5.1 | 4.2 | 5.2 | 5.2 |
| 1-kestose (%) | 0.0 | 35.9 | 53.1 | 57.3 | 46.6 | 37.5 | 26.5 | 22.6 | 19.2 |
| nystose (%) | 0.0 | 3.2 | 10.0 | 25.4 | 39.4 | 46.8 | 54.1 | 54.8 | 56.1 |
| fructosyl-nystose (%) | 0.0 | 0.0 | 0.0 | 0.0 | 2.6 | 4.2 | 8.5 | 10.1 | 12.3 |

TABLE 9

| | Maxazyme + catalase [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 0.6 | 1.0 | 1.3 | 1.7 | 2.4 | 2.7 | 3.1 | 3.5 |
| glucose (%) | 0.0 | 4.9 | 4.6 | 3.3 | 2.1 | 1.0 | 0.8 | 0.6 | 0.5 |
| sucrose (%) | 100.0 | 62.6 | 43.1 | 21.6 | 9.7 | 4.9 | 4.0 | 3.1 | 3.2 |
| 1-kestose (%) | 0.0 | 29.8 | 45.8 | 58.8 | 59.3 | 47.1 | 36.3 | 28.4 | 21.7 |
| nystose (%) | 0.0 | 2.0 | 5.5 | 15.1 | 27.2 | 41.3 | 50.7 | 56.6 | 59.6 |
| fructosyl-nystose (%) | 0.0 | 0.0 | 0.0 | 0.0 | 0.0 | 3.3 | 5.5 | 8.3 | 11.6 |

TABLE 10

| | Maxazyme (catalase not added) [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 2.4 | 1.8 | 1.6 | 1.7 | 1.7 | 1.8 | 1.9 | 2.0 |
| glucose (%) | 0.0 | 11.4 | 14.2 | 16.0 | 17.2 | 17.9 | 18.7 | 19.2 | 20.2 |
| sucrose (%) | 100.0 | 41.7 | 27.0 | 18.6 | 13.9 | 12.0 | 10.3 | 9.2 | 9.1 |
| 1-kestose (%) | 0.0 | 39.0 | 47.3 | 49.3 | 48.3 | 46.8 | 43.3 | 40.8 | 36.8 |
| nystose (%) | 0.0 | 5.5 | 9.6 | 14.4 | 18.9 | 21.6 | 26.0 | 28.8 | 31.9 |
| fructosyl-nystose (%) | 0.0 | 0.0 | 0.0 | 0.0 | 0.0 | 0.0 | 0.0 | 0.0 | 0.0 |

TABLE 11

| | Bakezyme + catalase [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 0.6 | 0.8 | 1.2 | 1.6 | 2.1 | 2.4 | 2.7 | 3.3 |
| glucose (%) | 0.0 | 5.2 | 6.1 | 5.9 | 4.5 | 2.1 | 1.8 | 2.2 | 2.6 |
| sucrose (%) | 100.0 | 62.1 | 43.1 | 23.0 | 11.8 | 5.9 | 4.1 | 3.8 | 3.4 |
| 1-kestose (%) | 0.0 | 30.0 | 44.6 | 56.4 | 58.0 | 50.5 | 40.0 | 31.5 | 24.7 |
| nystose (%) | 0.0 | 2.2 | 5.5 | 13.4 | 23.5 | 36.9 | 47.1 | 53.2 | 56.8 |
| fructosyl-nystose (%) | 0.0 | 0.0 | 0.0 | 0.0 | 0.6 | 2.5 | 4.6 | 6.6 | 9.2 |

TABLE 12

| | Bakezyme (catalase not added) [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 2.0 | 2.0 | 2.1 | 2.1 | 2.4 | 2.6 | 2.7 | 3.0 |
| glucose (%) | 0.0 | 8.0 | 11.8 | 15.5 | 17.3 | 18.0 | 18.9 | 19.2 | 20.0 |
| sucrose (%) | 100.0 | 55.5 | 34.6 | 18.6 | 13.2 | 10.8 | 9.6 | 8.8 | 9.0 |
| 1-kestose (%) | 0.0 | 31.9 | 44.9 | 50.1 | 48.5 | 45.8 | 40.5 | 37.1 | 33.8 |
| nystose (%) | 0.0 | 2.6 | 6.8 | 13.6 | 18.9 | 23.1 | 27.1 | 30.1 | 32.2 |
| fructosyl-nystose (%) | 0.0 | 0.0 | 0.0 | 0.0 | 0.0 | 0.0 | 1.3 | 2.1 | 2.2 |

TABLE 13

| | Sumizyme GOP + catalase [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 2.0 | 2.4 | 2.1 | 1.9 | 2.9 | 2.9 | 3.4 | 4.2 |
| glucose (%) | 0.0 | 5.2 | 4.6 | 3.3 | 1.8 | 0.0 | 0.7 | 0.7 | 0.7 |
| sucrose (%) | 100.0 | 65.7 | 40.4 | 20.4 | 8.3 | 4.4 | 3.4 | 3.8 | 3.4 |
| 1-kestose (%) | 0.0 | 24.9 | 46.0 | 58.2 | 57.4 | 44.7 | 32.6 | 24.5 | 19.4 |
| nystose (%) | 0.0 | 2.2 | 6.6 | 16.0 | 30.7 | 43.5 | 53.3 | 56.8 | 58.7 |
| fructosyl-nystose (%) | 0.0 | 0.0 | 0.0 | 0.0 | 0.0 | 4.5 | 7.0 | 10.8 | 13.6 |

TABLE 14

| | Sumizyme GOP (catalase not added) [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 1.4 | 1.7 | 1.8 | 2.2 | 2.4 | 2.8 | 3.3 | 3.9 |
| glucose (%) | 0.0 | 5.9 | 4.9 | 3.6 | 2.2 | 1.3 | 0.0 | 0.0 | 0.0 |
| sucrose (%) | 100.0 | 61.7 | 42.3 | 21.3 | 8.4 | 4.8 | 3.4 | 3.2 | 3.3 |
| 1-kestose (%) | 0.0 | 28.7 | 45.1 | 57.6 | 56.1 | 46.3 | 33.5 | 25.7 | 20.0 |
| nystose (%) | 0.0 | 2.2 | 5.9 | 15.7 | 31.1 | 42.5 | 53.6 | 58.0 | 59.0 |
| fructosyl-nystose (%) | 0.0 | 0.0 | 0.0 | 0.0 | 0.0 | 2.6 | 6.8 | 9.7 | 13.8 |

TABLE 15

| | Sumizyme PGO + catalase [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 1.8 | 2.0 | 2.4 | 2.3 | 2.5 | 2.8 | 3.1 | 3.3 |
| glucose (%) | 0.0 | 3.7 | 4.5 | 4.8 | 2.7 | 1.2 | 1.6 | 2.7 | 3.4 |
| sucrose (%) | 100.0 | 64.2 | 37.0 | 17.2 | 7.5 | 4.1 | 3.2 | 3.5 | 3.6 |

TABLE 15-continued

| | Sumizyme PGO + catalase [reaction time (hr)] | | | | | | | | |
|---|---|---|---|---|---|---|---|---|---|
| | 0 | 1 | 2 | 3 | 4 | 5 | 6 | 7 | 8 |
| 1-kestose (%) | 0.0 | 28.1 | 48.8 | 57.7 | 54.6 | 43.6 | 32.4 | 24.7 | 21.2 |
| nystose (%) | 0.0 | 2.1 | 7.7 | 17.9 | 32.0 | 44.6 | 53.5 | 56.3 | 57.1 |
| fructosyl-nystose (%) | 0.0 | 0.0 | 0.0 | 0.0 | 1.0 | 4.1 | 6.5 | 9.6 | 11.3 |

TABLE 16

| | Sumizyme PGO (catalase not added) [reaction time (hr)] | | | | | | | | |
|---|---|---|---|---|---|---|---|---|---|
| | 0 | 1 | 2 | 3 | 4 | 5 | 6 | 7 | 8 |
| fructose (%) | 0.0 | 3.4 | 2.1 | 1.6 | 1.2 | 1.3 | 1.4 | 1.4 | 1.5 |
| glucose (%) | 0.0 | 7.6 | 11.8 | 15.7 | 18.2 | 19.7 | 20.8 | 21.5 | 22.2 |
| sucrose (%) | 100.0 | 60.5 | 41.7 | 26.4 | 18.0 | 14.2 | 11.8 | 10.9 | 10.0 |
| 1-kestose (%) | 0.0 | 26.1 | 39.4 | 46.7 | 48.9 | 48.0 | 46.0 | 43.2 | 40.7 |
| nystose (%) | 0.0 | 2.4 | 5.1 | 9.7 | 13.7 | 16.8 | 20.0 | 23.0 | 25.5 |
| fructosyl-nystose (%) | 0.0 | 0.0 | 0.0 | 0.0 | 0.0 | 0.0 | 0.0 | 0.0 | 0.0 |

With regard to HYDERASE 15 (Tables 7 and 8) and Sumizyme GOP (Tables 13 and 14), there was no significant change in the sugar compositions between the catalase added sections and the non-added sections. In each test section, the nystose content was 50% or more and the content of glucose which inhibits a fructose transfer reaction was maintained below 10%.

On the other hand, with regard to Maxazyme (Tables 9 and 10), Bakezyme (Tables 11 and 12), and Sumizyme PGO (Tables 15 and 16), the catalase added sections all showed nystose contents of more than 50%, while the catalase non-added sections showed nystose contents of less than 33%. Furthermore, the glucose content became 10% or more after 2 hours from the initiation of the reaction. The reason why the nystose contents are low in the catalase non-added sections is presumed to be that hydrogen peroxide generated by an action of glucose oxidase on glucose accumulates in the reaction mixture solutions, followed by generation of hydroxyl radical and the like in the reaction mixture solutions and deactivation of glucose oxidase by the hydroxyl radical and the like.

In addition, HYDERASE 15 and Sumizyme GOP are known to contain catalase as an auxiliary activity enzyme. Therefore, with regard to HYDERASE 15 and Sumizyme GOP, it is presumed that the generated hydrogen peroxide was decomposed by the activity of catalase which is an auxiliary activity enzyme in the enzyme preparation.

Example 5: Production of Nystose Crystal-Containing Powder (3): Study of Components which Inhibit Crystallization (1)

In the process of obtaining crystals in step (D), components which might affect crystallization were studied using model solutions to which were added gluconic acid, enzymes, and fructosyl-nystose (GF 4).

A nystose-containing fraction before crystallization was obtained in accordance with the steps (A), (B), and (C) of Example 1. However, the enzymatic reaction conditions were set as follows.

Enzymes used:

| β-fructofranosidase in Reference Example 1 | 4,382 U |
| glucose oxidase (HYDERASE 15) | 22,000 U |
| catalase (Leonet) | 100,000 U |

Substrate solution: 578 g of sucrose dissolved in 1350 g of distilled water (Brix 30)
Temperature: 30° C.
pH: 7.3
Air flow rate: 3 L/min
Stirring speed: 800 rpm
Reaction time: 24 hours
Electrodialysis: the end point is when electric conductivity of a desalted solution reaches 0.8 mS/cm or lower (that is, the gluconic acid concentration is adjusted to 0.1 to 2.0 wt %).

The sugar composition of the nystose-containing fraction was as follows: fructose, 2.6 wt %; glucose, 0 wt %; sucrose, 3.0 wt %; 1-kestose, 20.5 wt %; nystose, 62.0 wt %; and fructosyl-nystose, 11.9 wt %.

As model solution (1), there was prepared a sugar solution containing no fructosyl-nystose. Existing respective sugar components were dissolved in deionized water in the following composition: fructose, 3.6 wt %; sucrose, 1.7 wt %, 1-kestose, 32.2 wt %, and nystose 62.3 wt %.

As model solution (2), there was prepared a sugar solution containing a plenty of gluconic acid. The model solution (2) was obtained by adding 3.3 wt % of sodium gluconate (special grade reagent, produced by Wako Pure Chemical. Ind., Ltd.) to the model solution (1).

As model solution (3), there was prepared a sugar solution to which was added a deactivated enzyme solution. An enzyme solution was prepared by mixing the above-mentioned three kinds of enzymes to be used in the present Example 5 in the above-described proportion and dissolving the mixture in deionized water. The prepared enzyme solution was boiled sufficiently to be deactivated and, thereafter, was filtered by a 0.45 μm filter. The enzyme solution after filtration was added to model solution (1). The concentration of the enzyme solution contained in model solution (3) was adjusted so that it became equivalent to the enzyme units contained in the above-described nystose-containing fraction.

As model solution (4), there was prepared a sugar solution containing a plenty of fructosyl-nystose. Existing respective sugar components were dissolved in deionized water in the following composition: fructose, 5.4 wt %; glucose, 2.3 wt %; sucrose, 3.3 wt %; 1-kestose, 11.6 wt %; nystose 62.4 wt %; and fructosyl-nystose, 14.7 wt %.

In step (D), the nystose-containing fraction, and model solutions (1) to (4) were each concentrated by means of a rotary evaporator to a sugar solid concentration of 75 wt %. To each solution after concentration, seed crystals (nystose crystals) were added under stirring in an amount of 0.1 wt % relative to the sugar solid concentration to initiate crystallization. The temperature at the initiation of crystallization was set at 55° C. The temperature of the solution was decreased gradually over about 40 hours to as low as 40 to 45° C. to precipitate the crystals. After the crystallization operation, separation was performed by means of a small-sized centrifuge, and crystals remained on the filter cloth were dried under reduced pressure at 70° C. The recovery rate and purity of nystose were calculated. The results are shown in Table 17.

TABLE 17

| | | nystose-containing fraction | model solution (1) | model solution (2) | model solution (3) | model solution (4) |
|---|---|---|---|---|---|---|
| sugar composition (%) | fructose | 2.6 | 3.6 | 3.6 | 3.6 | 5.4 |
| | glucose | 0 | 0 | 0 | 0 | 2.3 |
| | sucrose | 3.0 | 1.7 | 1.7 | 1.7 | 3.3 |
| | 1-kestose | 20.5 | 32.2 | 32.2 | 32.2 | 11.6 |
| | nystose | 62.0 | 62.3 | 62.3 | 62.3 | 62.4 |
| | fructosyl-nystose | 11.9 | 0 | 0 | 0 | 14.7 |
| added component | gluconic acid | + | − | + | − | − |
| | enzyme | + | − | − | + | − |
| nystose crystal recovery rate (%) | | 11.0 | 39.3 | 41.5 | 40.1 | unable to recover |
| nystose crystal purity (%) | | 81.2 | 90.3 | 88.2 | 88.6 | − |

In the results of Table 17, with regard to model solution (4), practically no nystose crystals precipitated under the above-described conditions and, therefore, crystals could not be recovered. Furthermore, the nystose-containing fraction containing 11.9 wt % of fructosyl-nystose showed a low recovery rate of crystals, which was specifically 11%. On the other hand, model solutions (1) to (3) which did not contain fructosyl-nystose, showed good recovery rates of crystals, which specifically was about 40%, although they contained gluconic acid or the enzyme solution. From these results, it is thought that, when the content of fructosyl-nystose in the solution before crystallization is 12% or more, the recovery rate of the nystose crystals tends to decrease.

Example 6: Production of Nystose Crystal-Containing Powder (3): Study of Components which Inhibit Crystallization (2)

In the same manner as in Example 5, model solutions (5) to (9) having different nystose contents and fructosyl-nystose contents were prepared in the same manner as in Example 5, and effects thereof on the recovery rates and purity of nystose crystals were studied. The results are shown in Table 18.

TABLE 18

| | | model solution (5) | model solution (6) | model solution (7) | model solution (8) | model solution (9) |
|---|---|---|---|---|---|---|
| sugar composition (%) | fructose | 2.4 | 2.0 | 3.9 | 3.2 | 5.3 |
| | glucose | 1.3 | 1.5 | 1.4 | 1.5 | 2.3 |
| | sucrose | 2.8 | 2.3 | 2.7 | 2.7 | 3.2 |
| | 1-kestose | 38.5 | 32.7 | 21.3 | 25.5 | 15.3 |
| | nystose | 49.8 | 55.1 | 60.5 | 60.4 | 61.9 |
| | fructosyl-nystose | 5.1 | 6.4 | 10.2 | 6.6 | 12.0 |
| nystose crystal recovery rate (%) | | unable to recover | 36 | 38 | 40 | unable to recover |
| nystose crystal purity (%) | | − | 76 | 82 | 84 | − |

Table 18 shows that, when the nystose contents were 55 wt % or more and the fructosyl-nystose contents were 10.2 wt % or less, it was possible to recover nystose crystals in good recovery rates.

Example 7: Production of Nystose Crystal-Containing Powder (4): Effect of Gluconic Acid Content in Crystallization By performing processes in the same manner as in steps (A) and (B) of Example 1, there was obtained "solution 7" as a reaction mixture solution after filtration. The enzymatic reaction time of step (A) was set at 24 hours. By performing electrodialysis using the "solution 7" for 7.5 hours in accordance with step (C) of Example 1, there were obtained "nystose-containing fraction 7a" and "gluconic acid-containing fraction 7b" having electric conductivity of 0.8 mS/cm or less. Subsequently, the nystose-containing fraction 7a was concentrated by means of an evaporator until the solid content concentration thereof became 80 wt % to obtain a "mother liquor 71" as a solution after concentration. The sugar composition of the mother liquor 71 was as follows: fructose, 2.5 wt %; glucose, 0.5 wt %; sucrose, 2.3 wt %; 1-kestose, 23.9 wt %; nystose 61.6 wt %; and fructosyl-nystose, 9.2 wt %. The gluconic acid content of mother liquor 71 was 1.0 wt %.

To mother liquor 71, there was added a solution, obtained by concentrating the gluconic acid-containing fraction 7b by means of an evaporator until the solid content concentration thereof became 80 wt %, to prepare mother liquors having gluconic acid contents of 1.0, 5.0, 10, 20, and 40 wt %.

Step (D): To each mother liquor in the test sections shown in Table 19, seed crystals (nystose crystals similar to those of Example 1) of 0.1 wt % relative to the sugar solid concentration were added under stirring to initiate crystallization. The temperature at the initiation of crystallization was set at 55° C. The temperature of the solution was decreased gradually over about 40 hours to as low as 40 to 45° C. to precipitate the crystals. After the crystallization operation, separation of centrifugal syrup was performed by means of a small-sized centrifuge, and crystals remained on the filter cloth were dried under reduced pressure at 70° C. to obtain nystose crystals. With regard to solution 7, it was concentrated by means of a rotary evaporator until the sugar solid content concentration became 80 wt % and, thereafter, the same operation as in the mother liquor was performed to obtain nystose crystals. The sugar compositions, gluconic acid contents, and recovery rates of the crystals were respectively analyzed or calculated. The results are shown in Table 19.

TABLE 19

| test section | gluconic acid content in mother liquor (%) | sugar composition (%) | | | | | | gluconic acid content in crystals (W/W %) | recovery rate of crystals (%) |
|---|---|---|---|---|---|---|---|---|---|
| | | fructose | glucose | sucrose | 1-kestose | nystose | fructosyl-nystose | | |
| mother liquor 71 | 1.0 | 0.8 | 0 | 0.5 | 10.0 | 85.2 | 3.5 | 0.3 | 38.1 |
| mother liquor 75 | 5.0 | 1.0 | 0 | 0.7 | 9.4 | 84.1 | 4.8 | 1.0 | 34.6 |
| mother liquor 710 | 10.0 | 0.5 | 0.5 | 1.1 | 10.6 | 82.5 | 4.7 | 4.2 | 31.2 |
| mother liquor 720 | 20.0 | 0.8 | 0.3 | 1.0 | 10.3 | 82.0 | 5.6 | 18.6 | 17.0 |
| mother liquor 740 | 40.0 | | | | unable to crystallize | | | | |
| solution 7 | 40.0 | | | | unable to crystallize | | | | |

Table 19 shows that the nystose crystals could be obtained when the gluconic acid content of the solution used in step (D) was 1.0 to 20 wt % (mother liquors 71 to 720). However, when the gluconic acid content was 20 wt % (mother liquor 720), the recovery rate of the crystals decreased by about 10 percentage points than when the content was 10 wt % (mother liquor 710). Further, when electrodialysis was not performed as step (C) (solution 7), and when the gluconic acid content in the mother liquor was 40 wt % (mother liquor 740), the nystose crystals could not be obtained.

Step E: The obtained nystose crystals were subjected to water content adjustment in the same manner as in step (E) of Example 1 and, thereafter, were evaluated for changes in water content, fluidity, powder-blown-up phenomenon, and degrees of dispersion (refer to Example 2). The water content adjustment was performed by aging the crystals under relative humidity of 50% at 30° C. for 7 days. The results are shown in Table 20.

Furthermore, a panel of seven experts conducted sensory evaluation of the taste of the obtained nystose crystal-containing powder. Evaluation points were given in 10 ranks (1: strong to 10: weak) for sweetness and saltiness, respectively, and in 10 ranks (1: favorable to 10: unfavorable) for overall agreeableness of the taste. An average of the evaluation points of the seven people was calculated and represented in Table 20 as follows: an average value of 1 to 2, +++; 3 to 5, ++; 6 to 8, +: and 9 to 10, −.

TABLE 20

| test section | water content (%) | | | fluidity | powder-blown-up | degree of dispersion | taste | | |
|---|---|---|---|---|---|---|---|---|---|
| | day 0 | day 1 | day 7 | | | | sweetness | saltiness | overall |
| mother liquor 71 | 0 | 8.0 | 8.4 | 3-4 | − | 17.9 | +++ | − | +++ |
| mother liquor 75 | 0 | 8.0 | 8.3 | 3-4 | − | 19.0 | +++ | − | +++ |
| mother liquor 710 | 0 | 7.7 | 7.9 | 3-4 | − | 19.5 | ++ | ++ | + |
| mother liquor 720 | 0 | 6.9 | 7.1 | 4 | − | 19.6 | − | +++ | − |

Table 20 shows that, in the crystal-containing powder having nystose purity of 82 to 85%, the powder had fluidity suitable for handling and was suppressed in the powder-blown-up phenomenon (evaluation: 3 to 4, −) when the gluconic acid contents in the nystose crystals were 0.3 to 18.6 wt %. It also shows that the degrees of dispersion showed 17.9 to 19.6%. Further, it shows that the water contents of the crystal-containing powder were in a range of 7.1 to 8.4 wt %. However, when the gluconic acid content in the nystose crystals was 10 wt %, the powder exhibited saltiness as well as sweetness. Furthermore, when the gluconic acid content was 20 wt %, the powder scarcely showed sweetness but showed very strong saltiness. The crystal-containing powder of the present invention scarcely showed acidity.

The invention claimed is:

1. A nystose crystal-containing powder, wherein:
   the powder has a nystose content of 83 to 89 wt %;
   the powder comprises 0.2 to 18.6 wt % of gluconic acid relative to a total weight of nystose crystals contained in the powder; and
   the powder has a water content of 8.3 to 14 wt %.

2. The nystose crystal-containing powder according to claim 1, wherein the powder has a melting point of 128 to 150° C.

3. The nystose crystal-containing powder according to claim 1, wherein the powder has a dispersion degree of 10 to 21%.

4. The nystose crystal-containing powder according to claim 1, wherein the powder comprises 0.26 to 1.0 wt % of gluconic acid relative to the total weight of the nystose crystals.

5. A method for producing a nystose crystal-containing powder according to claim 1, comprising the steps of:

(A) generating nystose by reacting sucrose with an enzyme solution containing β-fructofuranosidase and glucose oxidase;
   (B) converting glucose in the reaction mixture solution into gluconic acid by glucose oxidase;
   (C) adjusting a gluconic acid content in the solution obtained by steps (A) and (B) to 0.1 to 20 wt %;

(D) obtaining nystose crystals from the solution obtained by step (C); and (E) adjusting a water content of the nystose crystals obtained by step (D).

6. The method according to claim 5, wherein the solution obtained by step (C) has a nystose content of 55 wt % or more and a fructosyl-nystose content of less than 12 wt %.

7. The method according to claim 5, wherein the adjustment of the gluconic acid content in step (C) is performed by electrodialysis.

8. The method according to claim 5, wherein step (B) further comprises a step of removing hydrogen peroxide, produced as a byproduct, by catalase.

9. The nystose crystal-containing powder according to claim 1, wherein the powder has a water content of 8.6 to 14 wt %.

10. The nystose crystal-containing powder according to claim 1, wherein the powder has a water content of 8.8 to 14 wt %.

11. The nystose crystal-containing powder according to claim 1, wherein the powder has a water content of 9 to 14 wt %.

12. The nystose crystal-containing powder according to claim 1, wherein the powder has a water content of 10 to 14 wt %.

* * * * *